US008470035B2

(12) United States Patent
Cruise et al.

(10) Patent No.: US 8,470,035 B2
(45) Date of Patent: Jun. 25, 2013

(54) HYDROGEL FILAMENTS FOR BIOMEDICAL USES

(75) Inventors: Gregory M. Cruise, Rancho Santa Margarita, CA (US); Michael J. Constant, Mission Viejo, CA (US); Michael E. Keeley, Huntington Beach, CA (US); Terrance T. Tran, Westminster, CA (US)

(73) Assignee: MicroVention, Inc., Tustin, CA (US)

( * ) Notice: Subject to any disclaimer, the term of this patent is extended or adjusted under 35 U.S.C. 154(b) by 0 days.

(21) Appl. No.: 12/340,544

(22) Filed: Dec. 19, 2008

(65) Prior Publication Data

US 2009/0164013 A1   Jun. 25, 2009

Related U.S. Application Data

(60) Provisional application No. 61/016,342, filed on Dec. 21, 2007.

(51) Int. Cl.
*A61F 2/02* (2006.01)

(52) U.S. Cl.
USPC ........................ 623/11.11; 523/115

(58) Field of Classification Search
None
See application file for complete search history.

(56) References Cited

U.S. PATENT DOCUMENTS

| 5,607,417 | A | 3/1997 | Batich et al. |
|---|---|---|---|
| 5,651,979 | A | 7/1997 | Ron et al. |
| 5,952,232 | A | 9/1999 | Rothman |
| 6,103,865 | A | 8/2000 | Bae et al. |
| 6,270,748 | B1 * | 8/2001 | Annan et al. ............... 424/9.322 |
| 6,878,384 | B2 | 4/2005 | Cruise et al. |
| 2002/0176880 | A1 | 11/2002 | Cruise et al. |
| 2003/0220245 | A1 | 11/2003 | Hubbell et al. |
| 2003/0232895 | A1 | 12/2003 | Omidian et al. |
| 2004/0059370 | A1 | 3/2004 | Greene et al. |
| 2004/0098028 | A1 | 5/2004 | Martinez |
| 2005/0119687 | A1 * | 6/2005 | Dacey et al. ................ 606/200 |
| 2005/0196426 | A1 * | 9/2005 | Cruise et al. ................ 424/426 |

FOREIGN PATENT DOCUMENTS

| EP | 0 809 519 B1 * | 12/1996 |
|---|---|---|
| WO | 91/16057 A1 | 10/1991 |
| WO | 94/03155 A1 | 2/1994 |
| WO | 98/43615 A1 | 10/1998 |
| WO | 00/38651 A1 | 7/2000 |
| WO | 03/043552 A1 | 5/2003 |
| WO | WO 03043552 A1 * | 5/2003 |

OTHER PUBLICATIONS

Almany, Biomaterials, 26 (2005) 2467-2477 "Biosynthetic hydrogel scaffolds made from fibrinogen and polyethylene glycol for 3D cell cultures".

Carelli V. et al., "Silicone microspheres for pH-controlled gastrointestinal drug delivery", 1999, International Journal of Pharmaceutics, V179, p. 73-83.

* cited by examiner

*Primary Examiner* — Susan Tran
*Assistant Examiner* — William Craigo
(74) *Attorney, Agent, or Firm* — K&L Gates LLP; Louis C. Cullman; Brian J. Novak

(57) ABSTRACT

Described herein are apparatus, compositions, systems and associated methods to occlude structures and malformations with radiopaque hydrogel filaments with delayed controlled rates of expansion permitting the repositioning of the device once inside the structure or malformation. Further described is a device for implantation in an animal comprising a difunctional, low molecular weight ethylenically unsaturated shapeable macromer; an ethylenically unsaturated monomer; and a radiopaque element, wherein said device contains no support members. Methods of forming such devices are also disclosed.

17 Claims, No Drawings

HYDROGEL FILAMENTS FOR BIOMEDICAL USES

CROSS REFERENCE TO RELATED APPLICATIONS

This application claims the benefit of U.S. provisional patent application No. 61/016,342, filed Dec. 21, 2007, the entire disclosure of which is incorporated herein by reference.

FIELD OF THE INVENTION

The present invention relates generally to medical treatment apparatus and methods, more particularly, hydrogel filaments visible under x-ray fluoroscopy and magnetic resonance, and methods for use of such materials in biomedical treatment.

BACKGROUND

Presently, for patients suffering from cerebral and/or peripheral vascular disease, an interventional neuroradiologist/neurosurgeon has three main embolic device choices: platinum coils, hydrogel/platinum coils, or degradable polymer/platinum coils. All three types of coils are deployed into aneurysms and have advantages and disadvantages associated with them. Platinum coils are easy to deploy through standard microcatheters, are available in wide ranges of softness, and are best suited for aneurysms with small sizes or necks. Hydrogel/platinum coils are also easy to deploy through standard microcatheters. Although hydrogel/platinum coils are relatively stiffer than platinum coils and can be challenging to deploy inside aneurysms, they give acceptable results in a broader range of sac and neck sizes. Degradable polymer/platinum coils are easily tracked and deployed into aneurysm sacs; however, they only give acceptable results in aneurysms with small sizes or necks.

Despite the three coil varieties, there exists an unmet clinical need for embolic devices that deploy easily into aneurysm sacs (like platinum coils) and result in durable occlusion in a wide variety of aneurysm sizes (like hydrogel/platinum coils). Among the benefits of the apparatus and methods of the present description is a device that tracks through a microcatheter with less friction than a platinum coil, deploys in the aneurysm sac like the softest platinum coil on the market, expands like the hydrogel/platinum coils, and provides durable occlusion of the aneurysm sac, while permitting the interventional neuroradiologist/neurosurgeon, or surgeon, to use standard microcatheters and other associated equipment.

The improved durability of hydrogel/platinum coils is believed to be a result of the increased volumetric filling of the aneurysm sac and the resulting increase in stability of the coil mass. A current version of the hydrogel/platinum coil has an overcoil which limits the expansion of the hydrogel. In preclinical models, while current overcoiled hydrogel/platinum coils provide better results than platinum coils, it is believed that a non-overcoiled hydrogel device would be less stiff than current overcoiled versions. The present description provides an embolic device that is capable of providing increased volumetric filling, more so than both platinum coils and overcoiled hydrogel/platinum coils, with less stiffness than overcoiled hydrogel/platinum coils.

In large and giant aneurysms, inflammatory complications can occur, presumably due to the large amount of thrombus formation and organization. It is believed that with the increased volumetric filling of the aneurysm sac provided by the hydrogel, decreased thrombus formation and organization occurs and presumably fewer inflammatory complications result. The present description provides an embolic device which could reduce inflammatory complications.

An uncommon, but potentially dangerous, complication occurs when a coil gets interlocked within the winds of the coil itself. In this case, one can neither push nor pull the coil while keeping the device intact within the aneurysm site. The only option is to pull back and unwind the coil from the aneurysm site to the groin. The potentially dangerous result is a stretched coil. Although stretch resistant coils have been developed, this complication has not been eliminated, and still poses a dangerous threat to a patient. It is believed that the device of the present description eliminates this complication altogether.

SUMMARY

Described herein are apparatuses, compositions, systems and associated methods to occlude structures and malformations in body lumens with hydrogel filaments with delayed controlled rates of expansion including one or more visualization agents permitting the repositioning of the device once inside the structure or malformation. The structures and malformations can be a result of any number of cerebral and/or peripheral diseases. Generally, the controlled rate of expansion is imparted through the incorporation of ethylenically unsaturated monomers with ionizable functional groups, (e.g. amines, carboxylic acids). For example, if acrylic acid is incorporated into the cross-linked polymeric network, the hydrogel is then incubated in a low pH solution to protonate the carboxylic acids. After the excess low pH solution has been rinsed away and the hydrogel dried, the hydrogel can be introduced through a microcatheter filled with blood or saline at physiological pH. The hydrogel cannot and will not expand until the carboxylic acid groups deprotonate. Conversely, if an amine-containing monomer is incorporated into the cross-linked network, the hydrogel is incubated in a high pH solution to deprotonate amines. After the excess high pH solution has been rinsed away and the hydrogel dried, the hydrogel can be introduced through a microcatheter filled with blood or saline at physiological pH. The hydrogel cannot and will not expand until the amine groups protonate.

In one embodiment described herein is a device for implantation comprising a difunctional, low molecular weight ethylenically unsaturated shapeable macromer; an ethylenically unsaturated monomer; and a visualization agent, wherein the device contains no support members. In one embodiment, the support members are metallic.

In one embodiment, the macromer has a molecular weight of about 100 grams/mole to about 5000 grams/mole. In another embodiment, the hydrogel is environmentally-responsive. In yet another embodiment, the ethylenically unsaturated monomer comprises one or more ionizable functional groups.

In one embodiment, the macromer comprises polyethylene glycol, propylene glycol, poly(tetramethylene oxide), poly(ethylene glycol)diacrylamide, poly(ethylene glycol)diacrylate, poly(ethylene glycol)dimethacrylate, derivatives thereof, or combinations thereof. In another embodiment, the ethylenically unsaturated monomer comprises N,N'-methylenebisacrylamide, N-vinyl pyrrolidinone, 2-hydroxyethyl methacrylate, derivatives thereof, or combinations thereof.

In one embodiment, the visualization agents include radiopaque elements comprising an aromatic ring having a single unsaturation point and at least one iodine atom, tantalum, barium, salts thereof, or combinations thereof. In one embodiment, the visualization agent an aromatic ring having a single unsaturation point and two iodine atoms. In one embodiment, the visualization agent comprises gadolinium or iron oxide to impart visibility under magnetic resonance imaging.

In one embodiment, the ethylenically unsaturated monomer and the visualization agent comprise 2,4,6-triiodophenyl penta-4-enoate, 5-acrylamido-2,4,6-triiodo-n,n'-bis-(2,3 dihydroxypropyl) isophthalamide, derivatives thereof, or combinations thereof.

In one embodiment, the polymerization of the macromer and the monomer is initiated by N,N,N',N'-tetramethylethylenediamine, ammonium persulfate, azobisisobutyronitrile, benzoyl peroxides, 2,2'-azobis(2-methylpropionamidine)dihydrochloride, derivatives thereof, or combinations thereof.

In one embodiment, the ionizable functional groups comprise acidic groups or basic groups. In one embodiment, the basic group comprises amine groups, derivatives thereof, or combinations thereof. In another embodiment, the acidic groups comprise a carboxylic acid, derivatives thereof, or combinations thereof.

In one embodiment, the hydrogel is substantially free of acrylamide. In another embodiment, the hydrogel is substantially non-bioresorbable. In another embodiment, the hydrogel is bioresorbable.

One embodiment described herein is a method for preparing a device for implantation in an animal comprising: a) combining a difunctional, low molecular weight ethylenically unsaturated shapeable macromer; an ethylenically unsaturated monomer; a visualization agent, and a solvent to prepare a prepolymer solution; and b) treating the prepolymer solution to prepare a hydrogel that is expansible at physiological conditions.

In one embodiment of the method, the solvent comprises water, dichloromethane, acetone, isopropyl alcohol, ethanol, or combinations thereof. In another embodiment, the difunctional, low molecular weight ethylenically unsaturated shapeable macromer has a molecular weight of about 100 grams/mole to about 5000 grams/mole. In yet another embodiment, the ethylenically unsaturated monomer comprises ionizable functional groups.

In one embodiment of the method, solvent comprises about 20% w/w to about 80% w/w of the prepolymer solution. In another embodiment, the monomer comprises about 40% to about 80% by weight of the prepolymer solution.

In one embodiment, the method further comprises the step of adding a second an ethylenically unsaturated monomer to the prepolymer solution.

In one embodiment of the method, the ionizable functional groups comprise basic groups and the treating step comprises de-protonating the basic groups at pHs greater than the pKa or protonating the basic groups at pHs less than the pKa of the basic groups. In another embodiment of the method, the ionizable functional groups comprise acidic groups and the treating step comprises protonating the acidic groups at pHs less than the pKa or de-protonating the acidic groups at pHs greater than the pKa of said acidic groups.

In another embodiment, a device is described for implantation comprising: a difunctional, low molecular weight ethylenically unsaturated shapeable macromer with a molecular weight of about 100 grams/mole to about 5000 grams/mole; an ethylenically unsaturated monomer; and a visualization agent, wherein the device contains no metallic support members.

DETAILED DESCRIPTION

Described herein are apparatuses, compositions, systems and associated methods for occluding structures and malformations resulting from one or more cerebral and/or peripheral vascular diseases. Hydrogel filaments comprising one or more visualization agents having delayed, controlled rates of expansion are used to treat these structures and malformations, thereby permitting the repositioning of the device once inside the structure or malformation. Further, the hydrogel filaments including one or more visualization agents, for example radiopaque elements or fillers, with controlled rates of expansion give a surgeon a sufficient amount of time to properly position the filament without the need to rush as a result of immediate filament expansion.

Generally, the controlled rate of expansion of the hydrogel filaments is imparted through the incorporation of ethylenically unsaturated monomers with ionizable functional groups, (e.g. acidic or basic groups). For example, if acrylic acid is incorporated into the cross-linked polymeric network, the hydrogel is incubated in a low pH solution to protonate acidic, carboxylic acids. After the excess low pH solution has been rinsed away and the hydrogel dried, the hydrogel can be introduced through a microcatheter filled with blood or saline at physiological pH. The hydrogel cannot and will not expand until the carboxylic acid groups deprotonate. Conversely, if a basic, amine containing monomer is incorporated into the cross-linked network, the hydrogel is incubated in a high pH solution to deprotonate amines. After the excess high pH solution has been rinsed away and the hydrogel dried, the hydrogel can be introduced through a microcatheter filled with blood or saline at physiological pH. The hydrogel cannot and will not expand until the amine groups are protonated.

In one embodiment, whether acidic or basic groups are utilized on the monomeric species according to the present description, the devices described herein are expansible at physiological conditions. Physiological condition as used herein means a condition having at least one environmental characteristic found within or on the human body. Such characteristics include isotonic environment, pH buffered environment, aqueous environment, a pH of about 7, or combinations thereof and can be found in, for example, an isotonic solution, water, blood, spinal fluid, plasma, serum, vitreous humor or urine.

In one embodiment generally described herein are devices for implantation comprising a difunctional, low molecular weight ethylenically unsaturated shapeable macromer; an ethylenically unsaturated monomer; and a visualization element, wherein the device contains no support members. In one embodiment, the device contains one or more support members, but those support members are not metallic. Non-metallic support members can be polymeric. In one embodiment, the devices have one or more non-radiopaque or visualizable support members. In some embodiments, support members are not needed in the devices described herein to control expansion of the hydrogel, and as such, they are not incorporated into the apparatus and systems described herein.

Further, the absence of metallic support members from the devices described herein allow for better resolution under various imaging procedures. Metallic support members, for example, can distort the imaging of a device by producing flares or reflections from the metallic support members within the image. As such, providing a device with no metallic support members, but including one or more visualization agents, such as radiopaque elements or fillers, as taught herein allows one skilled in the art to attain a more precise and accurate image of the device both during and after implantation. Such devices with no metallic support members may include support members not visible to imaging techniques, for example polymeric support members.

In another embodiment described herein is a method for preparing a device for implantation in an animal comprising the steps of combining a difunctional, low molecular weight ethylenically unsaturated shapeable macromer; an ethylenically unsaturated monomer; a visualization element, and a solvent to prepare a prepolymer solution; and treating the prepolymer solution to prepare hydrogel that is expansible at physiological conditions.

Generally, the prepolymer solution is comprised of a solvent, a difunctional, low molecular weight ethylenically unsaturated macromer, an ethylenically unsaturated monomer with one or more visualization agents, an ionizable ethylenically unsaturated monomer, one or more optional ethylenically unsaturated monomers with visualization agents either with or without radiopacity, and an optional porosigen. Alternatively, the prepolymer solution is comprised of a solvent, a difunctional ethylenically unsaturated macromer, optional ethylenically unsaturated monomer or monomers, optional cross-linkers, and one or more visualization agents, such as radiopaque elements or fillers, which include, but are not limited to, barium, tantalum, platinum, and gold.

The solvent in the prepolymer solution serves to completely dissolve all macromers and monomers within the prepolymer solution. If a liquid monomer (e.g. 2-hydroxyethyl methacrylate) is used, a solvent may not be necessary. The solvent, if necessary, is selected based on the solubility of the macromers and monomers. Preferred solvents are isopropyl alcohol (IPA, isopropanol), ethanol, water, dichloromethane, and acetone; however, a number of other solvents could be utilized and are know to those skilled in the art. Preferred solvent concentrations range from about 20% w/w to about 80% w/w of the prepolymer solution, more preferably about 40% w/w to about 60% w/w. In one preferred embodiment, the solvent concentration is about 33% w/w of the prepolymer solution.

The difunctional low molecular weight ethylenically unsaturated shapeable macromer serves to cross-link the polymer chains during polymerization and impart flexibility to the resulting polymer. Such macromers include at least one ethylenically unsaturated group and two functional sites. In one embodiment, at least one ethylenically unsaturated group can be one of the functional sites, or can be both functional sites. In one embodiment, the macromers described herein have a low molecular weight. The macromers described herein have a molecular weight ranging from about 100 g/mol to about 5,000 g/mole, or about 200 g/mole to about 2,500 g/mole, more preferably about 400 g/mole to about 1,000 g/mole. A preferred macromer is poly(ethylene glycol)diacrylamide because of its biocompatibility and solubility in a wide variety of solvents. If degradation of the resulting polymer is desired, a preferred macromer is poly(ethylene glycol) diacrylate. Alternatively, more hydrophobic macromers such as the polyethers poly(propylene glycol) and poly(tetramethylene oxide) or derivatives of polyolefins such as poly(ethylene) are suitable. Other suitable macromers include polyethylene glycol, propylene glycol, and poly(ethylene glycol) dimethacrylate.

"Ethylenically unsaturated" as used herein generally describes a compound with a group such as, but not limited to, vinyl, acrylate, methacrylate, or acrylamide groups including derivatives thereof or combinations thereof.

A "shapeable" macromer is used herein to describe the relative rigidity of the macromer and its ability to hold a particular shape. For example, a shapeable macromer according to the present description can be formed using a device such as a mandrel and can hold the resulting shape for implantation.

The ethylenically unsaturated monomers with one or more visualization agents serve to impart visualization of the resulting polymer under the appropriate visualization method. In one embodiment, ethylenically unsaturated monomers comprise radiopaque elements or radiopaque elements alone which serve to impart radiopacity to the resulting polymer. Aromatic rings with single unsaturations and one or more iodine atom are preferred ethylenically unsaturated monomers with radiopaque elements. Examples include 2,4, 6-triiodophenyl penta-4-enoate and 5-acrylamido-2,4,6-triiodo-n,n'-bis-(2,3 dihydroxypropyl) isophthalamide. Preferred concentrations of the unsaturated monomer with radiopaque elements range from about 40% w/w to about 80% w/w of the prepolymer solution, more preferably about 40% w/w to about 60% w/w of the prepolymer solution. Alternatively, radiopaque elements or fillers such as tantalum, barium or salts thereof can be incorporated into the prepolymer solution either in place of the radiopaque elements or in addition to them. Radiopaque filler loadings range from about 40% w/w to about 60% w/w of the resulting polymer.

"Visulaization agent" as used herein refers to any element that is added to or encompassed within the devices described herein that impart a means of visualizing the device either during or after implantation. Methods of visualization include, but are not limited to, x-rays, ultrasound, fluoroscopy, infrared radiation, ultraviolet light methods, magnetic resonance and combinations thereof. In one embodiment, the visualization agent can be one or more radiopaque elements or fillers which impart radiopacity to the devices described herein. In another embodiment, the visualization agent can be a non-radiopaque element or filler such as gadolinium or iron oxide. Such non-radiopaque elements or fillers do not impart radiopacity to the devices described herein and can be imaged by, for example, magnetic resonance.

"Radiopaque" as used herein refers to elements or fillers as described above that impart radiopacity to the devices described herein and are detectable by a means of electrometric radiation such as, but not limited to, x-rays, ultrasound, fluoroscopy, infrared, ultraviolet and combinations thereof. In one embodiment, radiopaque elements described herein are detectable using x-rays or x-ray fluoroscopy.

The ionizable ethylenically unsaturated monomer serves to delay the expansion of the hydrogel filament, thereby establishing a controlled rate of expansion. In one embodiment, at least a portion, preferably about 5% to about 50% w/w of the monomer solution, more preferably about 5% to about 25% w/w of the prepolymer solution, of the monomers selected are ionizable. The preferred ionizable monomers may be acrylic acid or methacrylic acid. Derivatives and salts of both acids are also suitable ionizable components. Alternatively, in one embodiment, ionizable ethylenically unsaturated monomers are not utilized.

In one embodiment optional ethylenically unsaturated monomers with a visualization agent that does or does not impart radiopacity to the devices are used to aid the polymerization process and can be any mono or multifunctional ethylenically unsaturated compound. In one embodiment, ethylenically unsaturated monomers with visualization agents without radiopacity with low molecular weights are preferred. Hydroxyethyl methacrylate (e.g. 2-hydroxyetyl methacrylate), hydroxyethyl acrylate, N-vinyl pyrrolidinone and N,N'-methylenebisacrylamide are preferred ethylenically unsaturated monomers visualization agents without radiopacity. Preferred concentrations of the ethylenically unsaturated monomers visualization agents without radiopacity are less than about 5% w/w, more preferably less than about 1% w/w of the prepolymer solution.

In one embodiment, the hydrogels and devices described herein further comprise visualization agents, such as, gadolinium or iron oxide in addition to radiopaque elements to impart visibility of the devices under magnetic resonance imaging. In other embodiments, the gadolinium or iron oxide are used instead of or in place of the radiopaque elements.

The optional porosigen serves to impart pores in the resulting polymer. The porosity of the hydrogel material is imparted as a result of a supersaturated suspension of a porosigen in the prepolymer solution. A porosigen that is not soluble in the prepolymer solution, but is soluble in the washing solution, can also be used. In one embodiment, sodium chloride is the preferred porosigen. In other embodiments, ice, sucrose, and sodium bicarbonate can also be used as porosigens. It is preferred that the particle size of the porosigen be less than about 25 microns, more preferably less than about 10 microns. The small particle sizes aid the suspension of the porosigen in the solvent. Preferred concentrations of the porosigen are less than about 50% w/w, more preferably less than about 20% w/w of the prepolymer solution. In some embodiments according to the present description a porosigen is not utilized.

The prepolymer solution can be cross-linked by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the prepolymer solution.

In a preferred embodiment, the cross-linking method utilizes azobisisobutyronitrile (AIBN) or another water soluble AIBN derivative (2,2'-azobis(2-methylpropionamidine)dihydrochloride). Other cross-linking agents useful according to the present description include N,N,N',N'-tetramethylethylenediamine, ammonium persulfate, benzoyl peroxides, and combinations thereof, including azobisisobutyronitriles. In one embodiment, the AIBN or derivative thereof is used at an elevated temperature. After addition of AIBN, the prepolymer solution is injected into poly(ethylene) tubing with an inner diameter ranging from 0.012 inches to 0.075 inches and incubated for several hours at 80° C. The selection of the poly(ethylene) tubing imparts microcatheter or catheter compatibility. For delivery through microcatheters, poly(ethylene) tubing diameters from about 0.012 inches to about 0.025 inches are preferred. For delivery through 5 French Size (Fr) catheters, poly(ethylene) tubing diameters from about 0.030 inches to about 0.050 inches are preferred. Alternatively, HYTREL® (DuPont, Wilmington, Del.) tubing of the same diameter can be utilized. The HYTREL® tubing can be dissolved in solvents, facilitating removal of the polymer from the tubing.

If the poly(ethylene) tubing is wrapped around a mandrel prior to polymerization of the prepolymer solution, the resulting polymer will maintain the shape of the poly(ethylene) or HYTREL® tubing, primarily as a result of the shapeable macromer within the prepolymer solution. Using this technique, helical, tornado, and complex shapes can be imparted to the polymer. The memory of the imparted shape is strongly influenced by the macromer selection. More hydrophobic macromers retain their imparted shape better than more hydrophilic macromers. It is preferred that an ethylenically unsaturated shapeable macromer be used in this embodiment.

In one embodiment, the devices described herein are environmentally responsive. Environmentally responsive as used herein means that the devices change in some way in response to the surrounding environment. In one embodiment, this response to the surrounding environment is in the form of a controlled rate of expansion. A controlled rate of expansion of the hydrogels described herein is achieved through the protonation/deprotonation of ionizable functional groups present within or on the hydrogel network. Once the hydrogel has been prepared and the unincorporated macromers, monomers, and oligomers have been washed away, the steps to control the rate of expansion can be performed.

If monomers with carboxylic acid groups are incorporated into the hydrogel network, the hydrogel is incubated in a low pH solution. The free protons in the solution protonate the carboxylic acid groups within the hydrogel network. The length of incubation, temperature during incubation, and pH of the solution influence the amount of control on the expansion rate. Generally, the length and temperature of the incubation are directly proportional to the amount of expansion control, while solution pH is inversely proportional. Surprisingly, it was found that the water content of the treating solution also affects the expansion control. As the water content increases, the hydrogel is able to expand more in the treating solution and it is presumed that an increased number of carboxylic acid groups are available for protonation. An optimization of water content and pH can be required for maximum control of the expansion rate. After the incubation is concluded, the excess treating solution is washed away and the hydrogel material is dried. It has been observed that hydrogel treated with the low pH solution dries down to a smaller dimension than the untreated hydrogel. In one embodiment, smaller dimensioned hydrogels are utilized since delivery of these hydrogel materials through a microcatheter is desired.

In contrast, if pH sensitive monomers with amine groups are incorporated into or on the hydrogel network, the hydrogel is incubated in a high pH solution. Deprotonation occurs on the amine groups of the hydrogel network at high pH. The length of incubation, temperature during incubation, and pH of the solution influence the amount of control on the expansion rate. Generally, the length and temperature of the incubation and solution pH are directly proportional to the amount of expansion control. After the incubation is concluded, the excess treating solution is washed away and the hydrogel material is dried.

In some embodiments according to the present description, non-aqueous solvents are utilized. In such embodiments, monomers with protonated carboxylic acids (e.g., acrylic acid or methacrylic acid) can be used in place of their corresponding salts (e.g. sodium acrylate or sodium methacrylate). The use of these monomers in non-aqueous solvents obviates the need for subsequent treatment in low pH solutions.

After the cross-linked hydrogel has been washed, it is dried and a dried hydrogel filament is produced. The length can range from about 0.5 cm to about 100 cm and the diameter can range from about 0.010 inches to about 0.100 inches. In some embodiments, a pushable embolic device is required. In these instances, the dried hydrogel filament is loaded into introducer tubing, packaged, and sterilized. Upon receipt, the surgeon pushes the dried hydrogel filament into the microcatheter or catheter with a wire or other pusher. The dried hydrogel filament is then advanced down the microcatheter or catheter to the embolization site.

In one embodiment, the hydrogels described herein are substantially free of acrylamide. Consequently, the hydrogels substantially free of acrylamide have less than about 1% (w/w %) acrylamide per hydrogel mass. In other embodiments, the acrylamide is less than about 0.5% or less than about 0.01% of the hydrogel mass.

In other embodiments, the hydrogel is non-bioresorbable or substantially non-bioresorbable. A "non-bioresorbable" hydrogel as used herein is biocompatible and not subject to breakdown in vivo through the action of normal biochemical pathways. In one embodiment, the hydrogel is substantially non-bioresorbable and remains greater than 95% intact after 1 year of implantation. In other embodiments, the substantially non-bioresorbable hydrogel remains greater than 90% intact after 1 year.

In yet a further embodiment, the hydrogel is bioresorbable, meaning the hydrogel is biocompatible and is broken down in vivo through the action of normal biochemical pathways. In one embodiment, the hydrogel is bioresorbable and remains less than 5% intact after 1 year of implantation. In other embodiments, the hydrogel is bioresorbable and remains less than 5% intact after 2 years of implantation. In other embodiments, the hydrogel is bioresorbable and remains less than 5% intact after 5 years of implantation.

In another embodiment according to the present description, a retrievable embolic device is required. In these instances, a coupler is attached to a dried hydrogel filament by gluing, swaging, or other means known in the art. The coupler permits attachment to a delivery pusher. After attachment to the delivery pusher, the dried hydrogel filament/delivery pusher construct is packaged and sterilized. Upon receipt, a surgeon introduces the device into a microcatheter or catheter and advances it to the embolization site. The surgeon can retract and advance the device until it is positioned adequately. At this time, the surgeon can detach the dried hydrogel filament from the delivery pusher and remove the delivery pusher from the microcatheter or catheter.

In another embodiment, a fluid assisted injectable embolic device is used. In this case, a dried hydrogel filament is loaded into an introducer, packaged, and sterilized. Upon receipt, the surgeon injects the dried hydrogel filament into the microcatheter or catheter with a syringe filled with saline or other physiological solution. The saline or other physiological solution is used to assist in advancing the hydrogel filament down the catheter in addition to hydrating it. The dried hydrogel filament is then advanced down the microcatheter or catheter to the embolization site with subsequent injections.

EXAMPLES

The following are non-limiting examples of some of the biomedical applications of hydrogels with visualization agents described herein. It will be appreciated, however, that this material has many other medical and non-medical applications in addition to the specific examples set forth herein.

Example 1

Preparation of PEG 1000 Diacrylamide

First, 18 g of polyethylene glycol (PEG) 1000 was dried by azeotropic distillation with 200 mL of toluene. Then, 7.0 mL of triethylamine was added with 4.6 mL of mesyl chloride and stirred for 4 hr. The solution was then filtered to remove salt and the solvent evaporated. The resulting product was added to 150 mL of 25% ammonia hydroxide and stirred for 2 days. The water was removed and the product dried by azeotropic distillation with toluene. The resulting dried PEG diamine was dissolved in 20 mL dichloromethane and 50 mL toluene. Then, 7.0 mL of triethylamine and 4.9 mL of acryloyl chloride were added and the reaction proceeded for 4 hr while stirring. The resulting solution was filtered and the solvent was removed leaving PEG 1000 diacrylamide.

Example 2

Preparation of a Radiopaque Monomer

First, 9 g of triiodophenol was dissolved in 150 mL dichloromethane under argon. Then, 3.15 mL of pentenoyl chloride was added while stirring. Triethylamine was then added slowly and stirred for 4 hr. The solution was washed with 100 mL of water and evaporated to dryness, leaving 2,4,6-triiodophenyl penta-4-enoate.

Example 3

Preparation of a Radiopaque Hydrogel Filament in Chloroform

To prepare a radiopaque hydrogel in an organic solvent, 2 g of 2,4,6-triiodophenyl penta-4-enoate, 0.67 g of acrylic acid, 1.2 g of PEG diacrylamide 400, 24 mg of N,N-methylenebisacrylamide and 75 mg of azobis(2-methylpropionitrile) were dissolved in 2.5 mL of chloroform. Then, the solution was sparged with argon for 10 min before injection into a 0.020 inch polyethylene tubing using a 3 cc syringe. The tubes were heat sealed at both ends and placed in an 80° C. oven overnight to polymerize the solution.

Example 4

Preparation of a Barium Loaded Radiopaque Hydrogel Filament

To prepare a barium-loaded radiopaque hydrogel in an organic solvent, 7 g of barium sulfate, 0.5 g of acrylic acid, 5 g of poly(tetramethylene oxide)diacrylamide 1000, 1.25 g of 2-hydroxyethylmethacrylate, 212 mg of N,N-methylenebisacrylamide and 100 mg of azobis(2-methylpropionitrile) were dissolved in 3.5 mL of isopropyl alcohol. The solution was then sparged with argon for 10 min before injection into 0.010 inch HYTREL® tubing wrapped around a 4 mm mandrel using a 3 cc syringe. The tubes were heat sealed at both ends and placed in a 100° C. water bath for 1 hr, then overnight in an 80° C. oven to polymerize the solution.

Example 5

Preparation of a Radiopaque Hydrogel Filament in Water

To prepare a radiopaque hydrogel in water, 5 g of 2,5-acrylamido-2,4,6-triiodo-n,n'-bis-(2,3 dihydroxypropyl) isophthalamide, 1.33 g of acrylic acid, 2.5 g PEG diacrylamide 400, 50 mg of n-vinyl-2-pyrrolidinone and 100 mg of 2,2'azobis(2-methylpropionamidine)dihydrochloride were dissolved in 10 mL of water. The solution was then sparged with argon for 10 min before injection into 0.020 inch polyethylene tubing using a 3 cc syringe. The tubes were heat sealed at both ends and placed in an 80° C. oven overnight to polymerize the solution.

Example 6

Washing and Acid Treatment of a Radiopaque Hydrogel Filament

For the hydrogel polymerized according to Example 3, the tubes were cut into 3 inch sections and placed in acetone for 1 hr. In acetone, the hydrogel expanded out the ends of the tubes, allowing it to be removed from the tube. The hydrogel was washed in acetone for 2 hr. After 2 hr, the acetone was exchanged and the hydrogel was washed for another 2 hr. The acetone was removed and the hydrogel dried in a vacuum oven for 2 hr at 50° C.

For hydrogels polymerized according to Example 4, the hydrogel was removed by dissolving the tubing in a solution of 20% phenol in chloroform. After the tubing was dissolved, the phenol solution was exchanged with chloroform and washed for 1 hr. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

For the hydrogel polymerized according to Example 5, the tubes were cut into 3 inch sections and placed in the vacuum oven for 6 hr at 50° C. Once the hydrogel was dried, it can be pushed out of the tubes using a mandrel. The hydrogel was washed in water for 2 hr. After 2 hr the water was exchanged and the hydrogel was washed for another 2 hr. The water was removed and the hydrogel dried in a vacuum oven for 2 hr at 50° C.

Acid treatment of the hydrogels consisted of incubating in 1N hydrochloric acid (HCl) for 4 hr at 37° C. After 4 hr the acid was decanted off. The hydrogel was incubated in 99% isopropyl alcohol for 1 hr to remove any remaining acid. The hydrogel was dried in a vacuum oven for 1 hr at 50° C. to remove the remaining isopropyl alcohol.

Example 7

Attachment of a Radiopaque Hydrogel Filament to a Pusher

The radiopaque hydrogel filament can be attached to a V-TRAK® (MicroVention Terumo, Inc., Aliso Viejo, Calif.) or hydraulic pusher. To attach the hydrogel to a V-TRAK® pusher, a section of 0.0022 inch poly(ethylene) tubing suture was threaded through a coupler. The coupler consisted of a titanium cylinder hollowed out on one end and a through hole. The poly(ethylene) tubing suture was tied into a knot such that it could not be pulled back through. The hydrogel was glued into the coupler on top of the knot using adhesive. The other end of the poly(ethylene) tubing thread was threaded into a V-TRAK® pusher and tied.

To attach the hydrogel to a hydraulic pusher, a bullet coupler was used. The gel was glued into the coupler using adhesive and attached to a hydraulic pusher using heat shrink PET tubing.

Example 8

Measurement of Buckling Force

To compare the ability of the radiopaque hydrogel filament of Example 6 to deploy inside aneurysm sacs with other currently marketed coils, the buckling force of a variety of devices was determined. In this test, approximately one inch pieces of the devices were attached to about 15 inch pieces of hypo tubing by either soldering or poly(ethylene) shrink tubing. The hypo tubing end of the constructs was attached to an Instron 5543 Single Column Testing System, a system used to measure force data of materials. The construct was advanced down a dead end channel in a poly(carbonate) block. When the device reached the bottom of the channel, it was forced to buckle and the corresponding force was measured.

| Group | Buckling Force (gf) |
| --- | --- |
| HYPERSOFT ® Platinum Coil (MicroVention Terumo, Inc., Aliso Viejo, CA) | 0.6 ± 0.4 |
| MICROPLEX ® Platinum Coil 0.010 inch (MicroVention Terumo, Inc., Aliso Viejo, CA) | 2.3 ± 1.0 |
| HYDROCOIL ®10 (MicroVention Terumo, Inc., Aliso Viejo, CA) | 11 ± 4 |
| Radiopaque Hydrogel Filament | 0.5 ± 0.4 |

Three types of currently marketed coil systems were tested and compared to the radiopaque hydrogel filament of Example 6. The first coil tested was a HYPERSOFT® Platinum Coil. The HYPERSOFT® Platinum coil is a soft platinum finishing coil with an outer diameter of 0.012 inch and a filar size of 0.002 inch. The second coil tested was a MICROPLEX® Platinum Coil. The MICROPLEX® Platinum coil is a platinum filling coil with an outer diameter of 0.010 inch and a filar size of 0.002 inch. The HYPERSOFT® Platiumun coil and MICROPLEX® Platinum coil are soft platinum helical coils with no expandable hydrogel. The third coil tested was a HYDROCOIL® 10 system. The HYDROCOIL® 10 system is a platinum coil with an outer diameter of 0.008 inch and a filar size of 0.002 inch jacketed with an expandable poly(acrylamide-co-acrylic acid) hydrogel and overcoiled with a stretched platinum coil.

Statistically significant differences in the buckling force of the radiopaque hydrogel filament and the HYPERSOFT® Platiumun coil, an extremely soft platinum coil, were not observed. This experiment demonstrated that the radiopaque hydrogel filament has soft deployment characteristics suitable for embolic devices.

Example 9

Measurement of Bending Resistance

The bending resistance of the unexpanded hydrogel samples and the bending resistance of injectable platinum microcoils were obtained using a Gurley 4171ET tubular sample stiffness tester with a 5 g counterweight attached to its measuring vane. The sample length was one inch. The average of three replicates each are summarized in the following table.

| Sample | Measured Resistance (mg) |
| --- | --- |
| D-51 radiopaque hydrogel filament | 0.9 ± 0.4 |
| 0.008 inch platinum microcoil | 0.6 ± 0.2 |

The results illustrate little difference in relative stiffness between the radiopaque hydrogel filament and the platinum microcoil. The results demonstrate that the flexibility of an injectable platinum coil can be achieved with a radiopaque hydrogel filament.

Example 10

Evaluation of an Injectable Radiopaque Hydrogel Filament

Devices constructed from barium loaded radiopaque hydrogel formulations were evaluated in a flow model fitted with a torturous vessel. A flow directed microcatheter (Boston Scientific Spinnaker 1.5 F) was placed in the vessel. Devices ranging from 5 cm to 30 cm in length were injected through the microcatheter using a 3 cc syringe. The devices were evaluated on introduction, tracking, deployment and packing. To achieve a pass for Intro, Tracking, and Deploy, the implant must introduce, track and deploy using a 3 cc syringe without incident. To achieve a pass for packing, the implant must pack in a torturous vessel similar to a 0.008 inch platinum coil.

| Formulation | Intro | Tracking | Deploy | Packing |
|---|---|---|---|---|
| D-51 radiopaque hydrogel filament | Pass | Pass | Pass | Pass |
| 0.008 inch platinum coil | Pass | Pass | Pass | Pass |

The results illustrate that the radiopaque hydrogel filaments can be deployed into a simulated use torturous path and perform consistent with other embolic devices such as platinum coils.

Example 11

Evaluation of Radiopaque Polymer Hydrogel in Experimental Aneurysms

Three rabbit elastase aneurysms were embolized with radiopaque polymer filaments. The aneurysm width, length, and neck ranged from 2.4 to 3.6 mm, 4.7 to 8.8 mm, and 2.4 to 4.2 mm, respectively. A microcatheter (Cordis RAPIDTRANSIT®, Cordis Corporation, Miami Lake, Fla.) was placed inside the aneurysm sac. One to three radiopaque hydrogel filaments were deployed inside the aneurysm sac. Angiography demonstrated complete occlusion of all three aneurysms as a result of the embolization. At 6 wk post-embolization, complete occlusion of all three aneurysms was demonstrated by angiography. The aneurysms were harvested and histologically processed. The sections demonstrated complete filling of the aneurysm sac with the radiopaque hydrogel filaments, organizing/organized fibrous tissue in the clefts between the radiopaque hydrogel filaments, and an inflammatory response consisting of macrophages and a few giant cells. These results illustrated that the radiopaque hydrogel filaments can be deployed into experimental aneurysms and elicit a foreign body response consistent with other embolic devices.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A device for implantation comprising:
   a hydrogel filament comprising a difunctional, low molecular weight ethylenically unsaturated shapeable macromer;
   an ethylenically unsaturated monomer; and
   a visualization agent,
   wherein said device contains no support members and wherein the hydrogel filament has a buckling force of 0.5±0.4 gf.

2. The device according to claim 1 wherein said macromer has a molecular weight of about 100 grams/mole to about 5000 grams/mole.

3. The device according to claim 1 wherein said hydrogel filament is environmentally-responsive.

4. The device according to claim 1 wherein said macromer comprises polyethylene glycol, propylene glycol, poly(tetramethylene oxide), poly(ethylene glycol)diacrylamide, poly(ethylene glycol)diacrylate, poly(ethylene glycol) dimethacrylate, derivatives thereof, or combinations thereof.

5. The device according to claim 1 wherein said ethylenically unsaturated monomer comprises one or more ionizable functional groups.

6. The device according to claim 1 wherein said ethylenically unsaturated monomer comprises N,N'-methylenebisacrylamide, N-vinyl pyrrolidinone, 2-hydroxyethyl methacrylate, derivatives thereof, or combinations thereof.

7. The device according to claim 1 wherein said visualization agent comprises an aromatic ring having a single unsaturation point and at least one iodine atom.

8. The device according to claim 1 wherein said visualization agent comprises gadolinium or iron oxide.

9. The device according to claim 1 wherein said ethylenically unsaturated monomer and said visualization element comprise 2,4,6-triiodophenyl penta-4-enoate, 5-acrylamido-2,4,6-triiodo-n,n'-bis-(2,3 dihydroxypropyl) isophthalamide, derivatives thereof, or combinations thereof.

10. The device according to claim 1 wherein said macromer and said monomer are crosslinked with N,N,N',N'-tetramethylethylenediamine, ammonium persulfate, azobisisobutyronitrile, benzoyl peroxides, 2,2'-azobis(2-methylpropionamidine)dihydrochloride, derivatives thereof, or combinations thereof.

11. The device according to claim 1 wherein said ethylenically unsaturated monomer includes one or more ionizable functional groups comprising basic groups or acidic groups.

12. The device according to claim 11 wherein said ionizable functional groups comprise amine groups, derivatives thereof, or combinations thereof.

13. The device according to claim 11 wherein said acidic groups comprise a carboxylic acid, derivatives thereof, or combinations thereof.

14. The device according to claim 1 wherein said hydrogel is substantially free of acrylamide.

15. The device according to claim 1 wherein said hydrogel is substantially non-bioresorbable.

16. The device according to claim 1 wherein said hydrogel is bioresorbable.

17. A device for implantation in an animal comprising:
   a hydrogel filament comprising a difunctional, low molecular weight ethylenically unsaturated shapeable macromer with a molecular weight of about 100 grams/mole to about 5000 grams/mole;
   an ethylenically unsaturated monomer; and
   a visualization agent, wherein said device contains no support members and wherein the hydrogel filament has a buckling force of 0.5±0.4 gf.

* * * * *